US012638389B2

(12) United States Patent
Alden et al.

(10) Patent No.: US 12,638,389 B2
(45) Date of Patent: May 26, 2026

(54) SYSTEMS AND METHODS FOR CHARACTERIZING ATMOSPHERIC EMISSIONS

(71) Applicant: The Regents of the University of Colorado, Denver, CO (US)

(72) Inventors: Caroline B Alden, Boulder, CO (US); Robert J. Wright, Boulder, CO (US); Sean C. Coburn, Longmont, CO (US); Gregory B. Rieker, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 19/271,577

(22) Filed: Jul. 16, 2025

(65) Prior Publication Data

US 2025/0341465 A1     Nov. 6, 2025

Related U.S. Application Data

(63) Continuation of application No. 18/268,219, filed as application No. PCT/US2021/063782 on Dec. 16, 2021, now Pat. No. 12,385,834.

(Continued)

(51) Int. Cl.
*G01N 21/39* (2006.01)
*G01N 33/00* (2006.01)

(52) U.S. Cl.
CPC ......... *G01N 21/39* (2013.01); *G01N 33/0075* (2013.01); *G01N 2021/399* (2013.01)

(58) Field of Classification Search
CPC .............. G01N 21/39; G01N 33/0075; G01N 2021/399
See application file for complete search history.

(56) References Cited

U.S. PATENT DOCUMENTS

| | | | |
|---|---|---|---|
| 6,337,940 B1 | 1/2002 | Lefevre | |
| 2003/0197870 A1 | 10/2003 | Bagwell et al. | |

(Continued)

OTHER PUBLICATIONS

Alden C.B. et al.; "Bootstrap inversion technique for atmospheric trace gas source detection and quantification using long open-path laser measurements"; Atmos. Meas. Tech., 11, pp. 1565-1582, 2018.

(Continued)

*Primary Examiner* — Jamil Ahmed
(74) *Attorney, Agent, or Firm* — Cozen O'Connor

(57) ABSTRACT

A method characterizes gas emissions inside an area bounded by first, second, third, and fourth paths. A first spectrometer transmits a first beam along the first path. The first beam is retroreflected back to the first spectrometer, where it is detected to obtain a first signal. A second spectrometer transmits a second beam along the second path. The second beam is retroreflected back to the second spectrometer, where it is detected to obtain a second signal. A third spectrometer transmits a third beam along the third path. The third beam is retroreflected back to the third spectrometer, where it is detected to obtain a third signal. A fourth spectrometer transmits a fourth beam along the fourth path. The fourth beam is retroreflected back to the fourth spectrometer, where it is detected to obtain a fourth signal. The four signals are processed to identify gas sources inside the area.

19 Claims, 11 Drawing Sheets

Related U.S. Application Data

(60) Provisional application No. 63/126,729, filed on Dec. 17, 2020.

(56) References Cited

U.S. PATENT DOCUMENTS

| | | |
|---|---|---|
| 2004/0211900 A1 | 10/2004 | Johnson |
| 2011/0038507 A1* | 2/2011 | Hager ................ G01N 21/3504 |
| | | 382/100 |
| 2016/0209325 A1 | 7/2016 | Kotidis et al. |
| 2018/0172580 A1 | 6/2018 | Bjorøy |
| 2019/0265123 A1 | 8/2019 | Rieker et al. |

OTHER PUBLICATIONS

Alden C.B. et al.; "Single-Blind Quantification of Natural Gas Leaks from 1 km Distance Using Frequency Combs"; Environ. Sci. Technol. 2019, 43, pp. 2908-2917.

Coburn S. et al.; "Regional trace-gas source attribution using a field-deployed dual frequency comb spectrometer: supplementary material"; Optica; Mar. 2018; pp. 1-4.

Coburn S. et al.; "Regional trace-gas source attribution using a field-deployed dual frequency comb spectrometer"; Optica; vol. 5, No. 4, Apr. 2018; pp. 320-327.

PCT/US2021/063782 International Search Report and Written Opinion dated Mar. 25, 2022, 15 pages.

* cited by examiner

SYSTEMS AND METHODS FOR CHARACTERIZING ATMOSPHERIC EMISSIONS

RELATED APPLICATIONS

This application is a continuation of U.S. patent application Ser. No. 18/268,219, filed Jun. 17, 2023, which is a 35 U.S.C. § 371 filing of International Application No. PCT/US2021/063782, filed Dec. 16, 2021, which claims priority to U.S. Provisional Patent Application No. 63/126,729, filed Dec. 17, 2020. Each of these aforementioned applications is incorporated herein by reference in its entirety.

STATEMENT REGARDING FEDERALLY SPONSORED RESEARCH OR DEVELOPMENT

This invention was made with government support under grant number DE-FE0029168 awarded by the U.S. Department of Energy. The government has certain rights in the invention.

BACKGROUND

The burning of natural gas emits fewer carbon emissions than the burning of coal, and thus a transition from coal to natural gas may help reduce or revert climate change. The United States is already the world's largest producer of natural gas, outputting over 37 trillion cubic feet in 2018. In the United States, natural gas represents approximately one-third of the nation's entire energy production, the most of any energy type. It is also one of the nation's largest energy sources for electrical generation.

Natural gas is predominantly methane, a potent greenhouse gas. The potency of a greenhouse gas is commonly measured by global warming potential (GWP), which quantifies how much heat the gas traps in the atmosphere, relative to carbon dioxide, over a specific time horizon. By definition, the GWP of carbon dioxide is one. The GWP of methane is 86 over 20 years, and 34 over 100 years.

Significant infrastructure has been constructed, both in the United States and abroad, to extract, process, transport, and utilize natural gas. This infrastructure includes wells and rigs for extraction, pipelines and liquid natural gas (LNG) tankers for transportation, liquification and condensation facilities, processing plants for removing impurities and non-methane components, storage tanks, and industrial boilers (e.g., refineries, power stations, chemical plants) that utilize methane as an energy source for generating heat.

Since methane is a gas, it can easily escape into the atmosphere through emission points that form in equipment and components, such as valves, pipes, connectors, pumps, pressure-relief devices, open-ended lines, and sampling connections. Emissions at a typical facility (e.g., refinery or chemical plant) may arise, for example, from seals and gaskets that are improperly seated or maintained. A typical facility has almost 20,000 valves and connectors, and may have over 100,000. Failure of any one of these components may result in an emission point. However, emission points may also arise from corrosion of metal components, as well as damage to components due to normal wear and tear and/or anomalous operation.

Therefore, to obtain the full environmental benefit of switching from coal to natural gas, it is beneficial to reduce the number of methane emission points and the quantity of methane emitted by each emission point. The amount of emitted methane (also known as "fugitive emissions") in the United States is estimated to be between 1.4% and 2.3% of total production per year. Equivalent to 0.5-0.8 trillion cubic feet, these fugitive emissions are enough to heat between 7 and 11 million homes.

In 2016, the United States Environmental Protection Agency (EPA) passed three new rules to help reduce methane emissions in the oil and natural gas industries. These rules include New Source Performance Standards that sets emission limits for methane and requires owners/operators of equipment to find and repair sources of fugitive methane emissions. The EPA estimates that these rules will reduce fugitive methane emissions by 510,000 short tons, or 23 billion cubic feet.

To adhere to the 2016 EPA rules, owners/operators of natural gas well sites, oil well sites, gathering and boosting stations, and compressor stations must survey their equipment for emissions at fixed schedules. Owners/operators must use optical gas imaging (OGI) to conduct these surveys. The most common type of OGI uses an infrared camera that is sensitive between 3.3 and 3.4 μm, where methane has absorption lines. However, the performance of an infrared camera depends on weather conditions (e.g., temperature, wind) as well as the emissivities of materials in the background of the image. As an alternative to OGI, owners/operators may invoke "Method 21" in which surveying is conducted with a portable instrument, such as an organic vapor analyzer.

The 2016 EPA rules also allow the EPA to approve the use of emerging technologies as alternatives to OGI; owners/operators must submit information demonstrating that the alternative technology is capable of achieving methane reductions equivalent to those that can be achieved when OGI or Method 21 is used to find and repair emission points.

In addition to the oil and gas industries, methane emissions are also of concern in agriculture, where global emissions from livestock is estimated at 119 Tg per year (equivalent to 5.9 trillion cubic feet). Other major anthropogenic sources of methane include methane-emitting bacteria that grow in rice paddies (estimated at 115-243 Tg emitted globally per year), biomass burning (estimated at 40-55 Tg emitted globally per year), and landfills (estimated at 40-55 Tg emitted globally per year).

SUMMARY

The present embodiments include methods for using optical gas detectors to characterize emissions from one or more potential or known gas sources. Specifically, optical beams (e.g., laser beams or incoherent light beams) propagate along various paths, after which they are detected to obtain path-integrated absorption measurements. In some of these embodiments, multiple paths are measured simultaneously with multiple spectrometers. In other embodiments, only one spectrometer is used to measure multiple paths sequentially. The paths are selected to either fully or partially bound a geographic area to be monitored. The geographic area may cover several square kilometers, or more, i.e., each laser beam may propagate for several kilometers, or more, before being detected.

The resulting absorption measurements may be combined with position information, environmental information (e.g., wind speed and direction, temperature, etc.), and other measurements (e.g., gas measurements performed with other instruments) to perform data analysis that outputs information about the emissions. For example, an inversion may be used to obtain background concentrations, gas source locations (e.g., center coordinates or constrained areas), identified species, plume parameters (e.g., mass, diffusivities, etc.), or a combination thereof. Without departing from the scope hereof, this data analysis may be used to determine additional or alternative information that characterizes the emissions.

Many of the present embodiments use retroreflected optical beams, which advantageously allows an optical beam to be detected at a location near where it is transmitted. Co-locating the apparatus for generating, transmitting, and detecting an optical beam (or multiple optical beams) allows sharing of equipment, which reduces cost and size of the optical gas detector. This approach also simplifies setup by allowing most of the equipment to be installed in a vehicle (e.g., a truck) that can be easily moved to different locations.

Any of the present embodiments may be implemented with a dual-frequency-comb spectrometer, a single-frequency laser spectrometer (e.g., tunable-diode laser absorption spectroscopy), or another type of optical spectrometer used to measure gas species via absorption of light (either coherent or incoherent). Examples of gas species that may be measured include, but are not limited to methane, acetylene, carbon dioxide, water vapor, carbon monoxide, hydrogen sulfide, ethylene, ethane, propane, butane, and BTEX (benzene, toluene, ethylbenzene, and xylene).

DETAILED DESCRIPTION

Figure 1:
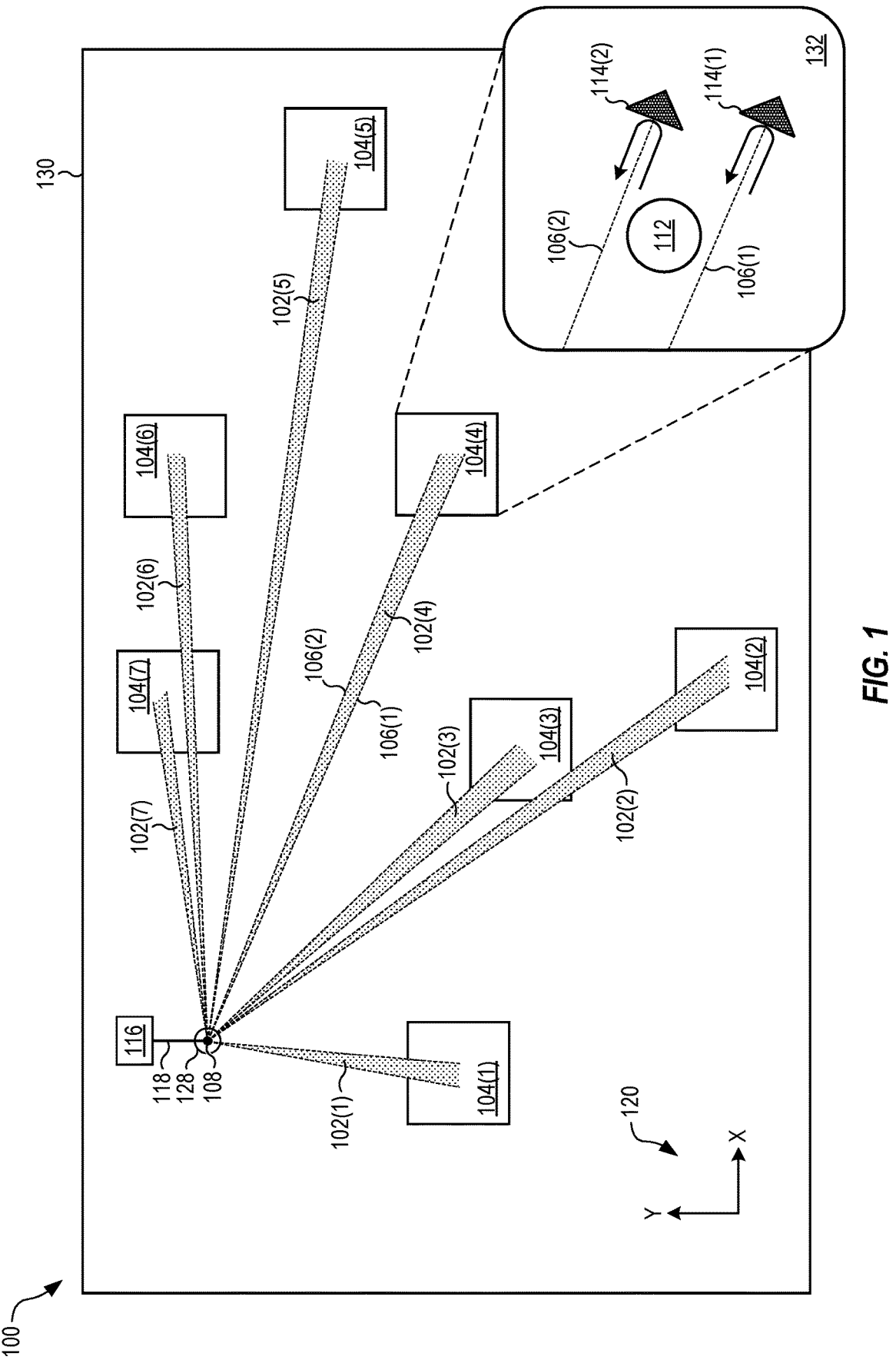
FIG. 1 shows a top view of an optical gas detector being used to remotely measure gases within a geographic area, in an embodiment.

FIG. 1 shows a top view of an optical gas detector 100 being used to remotely measure gases within a geographic area 130, in an embodiment. The gas detector 100 includes a spectrometer 116 that generates an optical beam and measures gas species via absorption of the optical beam after it is transmitted from, and reflected back toward, a center point 108. To transmit the optical beam in various directions (see right-handed coordinate system 120), the gas detector 100 may include a gimbal mount 128 located at the center point 108. In FIG. 1, the spectrometer 116 outputs light into a fiber-optic cable 118 that guides the light to the gimbal mount 128. Optics affixed to the gimbal mount 128 then couple the light into a free-space optical beam. Alternatively, all or part of the spectrometer 116 may be mounted directly to the gimbal mount 128.

The spectrometer 116 may be a dual-frequency-comb spectrometer, a single-frequency laser spectrometer (e.g., tunable-diode laser absorption spectroscopy), or another type of laser spectrometer used to measure gas species via absorption of laser light. In these embodiments, the optical beam is a beam of coherent light (e.g., a laser beam). In other embodiments, the spectrometer 116 generates and detects an optical beam of incoherent light. Examples of gas species that may be measured by the gas detector 100 include, but are not limited to methane, acetylene, carbon dioxide, water vapor, carbon monoxide, hydrogen sulfide, ethylene, ethane, propane, butane, and BTEX (benzene, toluene, ethylbenzene, and xylene). The geographic area may cover several square kilometers, or more, i.e., the optical beam may propagate for several kilometers, or more, before being reflected back to the center point 108.

In FIG. 1, the gimbal mount 128 steers the optical beam to measure gases within seven sectors 102 that spatially overlap seven corresponding pads 104. As shown in a detailed view 132 of a fourth pad 104(4), a first laser beam 106(1) is transmitted from the center point 108 to a first retroreflector 114(1) placed within, or near, the fourth pad 104(4). Alternatively, light may be reflected and return to center point 108 after scattering off of elements of the environment or other materials. The retroreflected first laser beam 106(1) returns to the center point 108, where it is detected by the laser spectrometer 116, which generates a resulting first absorption signal. A second laser beam 106(2) is then transmitted from the center point 108 to a second retroreflector 114(2) (or another scattering surface) placed within, or near, the fourth pad 104(4). The reflected second laser beam 106(2) returns to the center point 108, where it is also detected by the laser spectrometer 116, which generates a resulting second absorption signal. This process may be repeated one or more times. The first and second absorption signals, and any repeated absorption signals, may then be processed to determine one or more concentration levels of one or more species of gas within or near the sector 102(4), including at least part of the fourth pad 104(4). The paths along which the first and second laser beams 106(1), 106(2) propagate, and therefore which azimuthally bound the corresponding sector 102, may also be referred to herein as first and second rays, respectively. Each sector 102 is an example of what is referred to herein as a "monitored area".

The laser beams 106(1) and 106(2) may propagate on opposite sides of a piece of equipment 112 located within, or near, the pad 104(4). The piece of equipment 112 may be an oil well, pump, storage tank, or other item that could emit gas. The equipment 112 is therefore one example of a candidate emission source, or source of gas emitted into the atmosphere. As described in more detail below, under different wind conditions, the emitted gas will flow disproportionately through the two laser beams. For example, for certain wind properties (i.e., speeds and directions) the emitted gas will flow through only one of the two laser beams 106(1) and 106(2). This one laser beam is also referred to herein as the downwind laser beam. An absorption measurement performed with the downwind laser beam will show absorption features that are characteristic of one or more species present in the gas. Advantageously, the other of the two laser beams 106(1) and 106(2) can be used to obtain another absorption measurement that may, for example, indicate a background concentration of the one or more species. This other laser beam is also referred to herein as the upwind laser beam. This set of absorption measurements can be combined to improve the accuracy with which gas detected by the downwind laser beam can be attributed to originating at the equipment 112. Any disproportionate signature imposed on the two beams by the emitted gas source can be used to understand emissions from equipment 112 or other equipment near or outside this area.

Still referring to the fourth pad 104(4), the laser beams 106(1) and 106(2) define two edges of the sector 102(4), which originates at the center point 108. When the retroreflectors 114(1) and 114(2) (or other scattering surfaces) are located within, or near, the fourth pad 104(4), the sector 102(4) at least partially overlaps the fourth pad 104(4). The retroreflectors 114(1) and 114(2) (or other scattering surfaces) may be positioned differently than shown in the detailed view 132, and a pad 104 may include more than one piece of equipment 112 (i.e., more than one candidate emission sources). Equipment or pipelines outside of the pad may also be candidate emission sources that are monitored.

The above description applies to all seven pads 104 shown in FIG. 1. Accordingly, FIG. 1 shows seven corresponding sectors 102, all originating at the center point 108. The pads 104 measured by the spectrometer 116 may be located anywhere around the center point (i.e., in all 360 degrees). While the example of FIG. 1 shows seven pads 104 being monitored, a different number of pads 104 may be monitored without departing from the scope hereof and areas outside of pads 104 may also be monitored.

When the spectrometer 116 can transmit and detect only one laser beam at a time, a first absorption measurement performed with the first laser beam 106(1) precedes a second absorption measurement performed with the second laser beam 106(2). More specifically, the gas detector 100 controls the gimbal mount 128 to steer the first laser beam 106(1) at a first angle (e.g., relative to a reference direction, such as geodetic north or grid north). The gas detector 100 may then control the gimbal mount 128 to steer the second laser beam 106(2) at a second angle that is different from the first angle. When the spectrometer 116 can transmit and detect two laser beams simultaneously (e.g., two single-beam laser spectrometers operating in parallel, and located near the center point 108), the gas detector 100 can obtain the first and second absorption measurements by simultaneously transmitting the first laser beam 106(1) at the first angle and the second laser beam 106(2) at the second angle, and simultaneously detecting the corresponding first and second retroreflected (or otherwise returned or detected) laser beams 106(1), 106(2).

After the gas detector 100 performs one or more absorption measurements for one pad 104 and obtains a corresponding emission characterization (i.e., the gas detector 100 has "sampled" the one pad 104), the gas detector 100 may then control the spectrometer 116 and gimbal mount 128 to sample the next pad 104. In one embodiment, the gas detector 100 samples the pads 104 sequentially, i.e., in a fixed predetermined order. However, the gas detector 100 may sample the pads 104 in a different order without departing from the scope hereof.

In some embodiments, the gas detector 100 adaptively determines, in real-time, the next pad 104 to be sampled. Specifically, the gas detector 100, after sampling a first sector 102, may then determine a next sector 102 to sample by calculating a ranking score for each sector 102. The ranking score may be calculated based on one or more of the following data: wind orthogonality, site-specific wind constraints, an elapsed time since the sector 102 was last sampled, a measured emission history for the sector 102, one or more images of the sector 102 or corresponding pad 104, and sensor data obtained from the corresponding pad 104. Additional data may be used to determine each ranking score (or other method for determining order of sampling) without departing from the scope hereof. The gas detector 100 may then select, as the next sector 102 to sample, the one sector 102 with the highest ranking score. The gas detector 100 may then control the gimbal mount 128 to direct the first and second laser beams 106(1), 106(2) according to the first and second angle of the next sector 102. In place of a ranking score, another system to determine the sequence of visits may be used without departing from the scope hereof.

Advantageously, the ranking scores can be calculated to increase the likelihood that the inversion for the next sector 102 is successful, and that the gas detector 100 does not waste time sampling sectors 102 for which non-ideal conditions (e.g., meteorological conditions) exist. Scoring may utilize strict Boolean rules, a machine-learning algorithm, or another technique, or combination of techniques, for calculating scores based on the above-listed data. Selection may also occur without scoring (e.g., Boolean rules alone).

Figure 2:
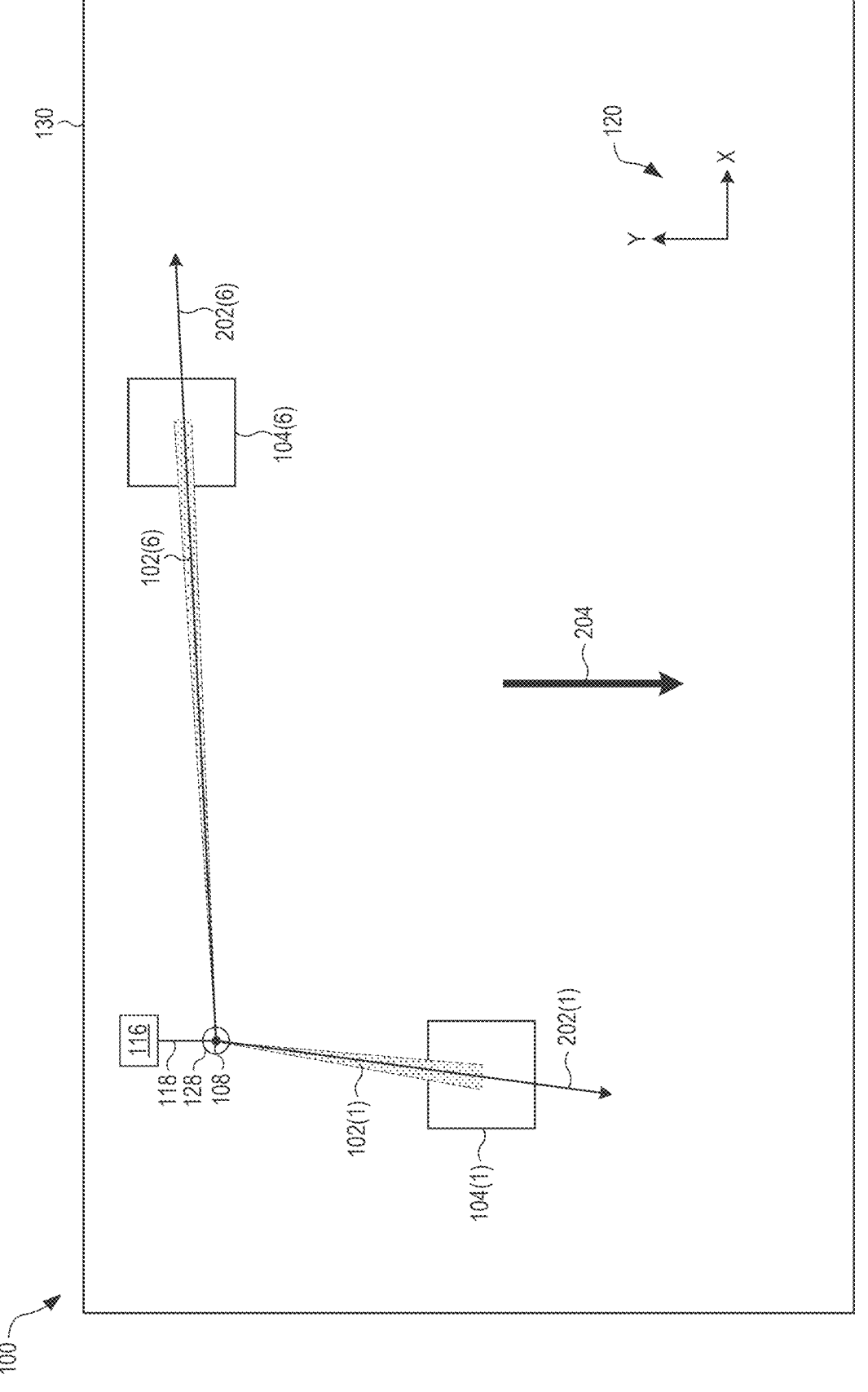
FIG. 2 illustrates wind orthogonality for the optical gas detector of FIG. 1, in an embodiment.

FIG. 2 illustrates wind orthogonality for the optical gas detector 100 of FIG. 1, in an embodiment. An inversion for a sector 102 is most likely to be successful when the wind direction is perpendicular to the first and second laser beams 106(1), 106(2) of the sector, as this reduces the likelihood that gas emitting from the equipment 112 will contaminate the upwind beam (or that the plume will miss the downwind beam), which is used to determine, or constrain, background concentrations. For clarity, only the first and sixth sectors 102(1), 102(6), and corresponding first and sixth pads 104 (1), 104(6), are shown in FIG. 2. Each sector 102(i) has a corresponding center ray 202(i) that originates at the center point 108 and forms an angle that is the average of the first and the second angles. Thus, each center ray 202 is azimuthally mid-way between the corresponding first and second laser beams 106(1), 106(2). Also shown in FIG. 2 is a vector indicating a wind direction 204 within the geographic area 130. The wind direction 204 may be measured (e.g., with an anemometer located within the geographic area 130) or calculated from meteorological data. Any differential influence of a plume from the equipment 112, or other areas on the first and second laser beams 106(1) and 106(2), is information that can be used to understand emissions from the equipment 112 or other areas.

In some embodiments, the wind orthogonality of a sector 102(i) is defined as the absolute value of the sine of the angle between the wind direction 204 and the center ray 202(i) of the sector 102(i). Thus, in the example of FIG. 2, the wind direction 204 is almost orthogonal (90 or 180 degrees) to the first center ray 202(1), and therefore the wind orthogonality of the first sector 102(1) is relatively high (i.e., close to one). On the other hand, the wind direction 204 is almost parallel to the sixth center ray 202(6), and therefore the wind orthogonality of the sixth sector 102(6) is relatively low (i.e., close to zero). Therefore, wind orthogonality may be used as a weight to preferentially increase the ranking scores of sectors 102 that have a wind direction 204 more perpendicular to the first and second laser beams 106(1), 106(2).

Site-specific wind constraints refer to wind data that may be used to assign a ranking score of zero to certain sectors 102 when one or more constraints are not met. A ranking score of zero effectively removes a sector 102 from consideration for the next sector 102. For example, in some situations, a sector 102 is sampled if the wind direction is within a certain angular range, if the wind speed is within a certain range of values, or both. If all of the one or more constraints for a sector 102 are met, then the sector 102 is assigned a site-specific wind score of one. Otherwise, the sector 102 is assigned a site-specific wind score of zero. An overall wind score for the sector 102 may be obtained by multiplying the site-specific wind score by the wind orthogonality. The ranking score for the sector 102 may then be calculated based on its overall wind score.

The determination of ranking scores may also be based on an elapsed time since each sector 102 was last sampled. For example, a ranking score for a sector 102 may be increased with the elapsed time, thereby preventing a large time gap between consecutive measurements of the sector 102.

The determination of ranking scores may also be based on a measured emission history for each sector 102. For example, the ranking score may be increased for a sector 102 within which high concentrations of certain species were recently measured. Such an emission history may indicate that the sector 102 contains one or more active emission sources, and that the gas detector 100 may sample the sector 102 more frequently to better track the evolution of the emission(s).

The determination of ranking scores may also be based on one or more images of each sector 102, its corresponding pad 104, and any equipment 112 located therein. The gas detector 100 may use these images, which may include telescopic images and satellite images, to determine the physical condition of the equipment 112. For example, the images may show damage, or another kind of abnormality, that could indicate a gas emission originating from the equipment 112. In such a situation, the sector 102 may be ranked highly so that the gas detector 100 can then quickly sample the sector 102 to determine if there is a gas emission. The one or more images may also include FLIR images that indicate gas emissions originating from the equipment 112, or elsewhere within the sector 102.

The determination of ranking scores may also be based on sensor data obtained locally or remotely. The sensor data may include pressure data, temperature data, flow-rate data, and other data typically recorded from the piece of equipment 112 or from related or connected equipment elsewhere. Such data may indicate an abnormality in the functioning of the equipment 112, even if the equipment 112 appears physically undamaged. An indication of abnormality could be the sign of a gas emission. In this case, the sector 102 may be ranked highly so that the gas detector 100 quickly samples the sector 102 to determine if there are conditions related to a potential gas emission originating with the equipment 112.

Estimation of Background Methane Concentration

To accurately detect and characterize a gas emission, knowledge of the background concentration of methane in the atmosphere is needed. This knowledge can come from a measurement, a model, or a combination thereof. The background concentration can vary in time and space, especially when local sources outside of the monitored area are also emitting gas. As such, it can be useful to disentangle the background concentration from enhancements in atmospheric concentrations due to plumes from known methane sources.

More than one sensor can be used to estimate either the background concentration or the downwind concentration (e.g., plume) of methane. In some embodiments, the more than one sensor includes multiple types of sensors. For example, on-site measurements of methane can be conducted with multiple, independent instruments (e.g., dual-comb spectroscopy, FLIR, airborne-based LIDAR, fixed point sensor, UAV-mounted sensor, etc.). Each of these instruments can be used to independently estimate methane flux. Crucially, they also sample different masses of air. Some of these air masses may have a plume at certain times, while at other times they may not have a plume, but there are circumstances in which the background methane concentrations are the same. By synchronizing concentration time series from two or more instruments, it is possible to significantly improve the estimate of the background methane concentration, even when one instrument is measuring inside of a plume. Separate measurements can also help constrain plume locations by measuring background or non-background concentrations.

Advantageously, measurements of background methane concentration using multiple types of sensors provide more information about the spatial and temporal characteristics of the background air, as compared to using only one type of sensor. This use of multiple sensor types can provide more robust estimates of enhancement signals, and can therefore increase confidence in emission characterization (e.g., detection, attribution, and quantification).

In some embodiments, the gas detector 100 can be used to calibrate point sensors, or other types of sensors, located remotely or through the geographic area 130. Here, a point sensor refers to a type of sensor that measures concentration at the location of the sensor (i.e., locally). By contrast, the gas detector 100 is an example of a line sensor that measures concentration (i.e., absorption) integrated along the optical path of the laser beam. The combination of point sensors and line sensors may be used to provide coverage of a region (e.g., the geographic area 130 of FIGS. 1 and 2), even if the data from the point sensors and the data from the line sensors are used independently, and used in conjunction.

In the preceding discussion, the gas species to be measured (both for emissions and background) is methane. However, the above embodiments apply to any type of gas species that can be measured by the gas detector 100.

Transmit/Receive Configurations

Figure 3:
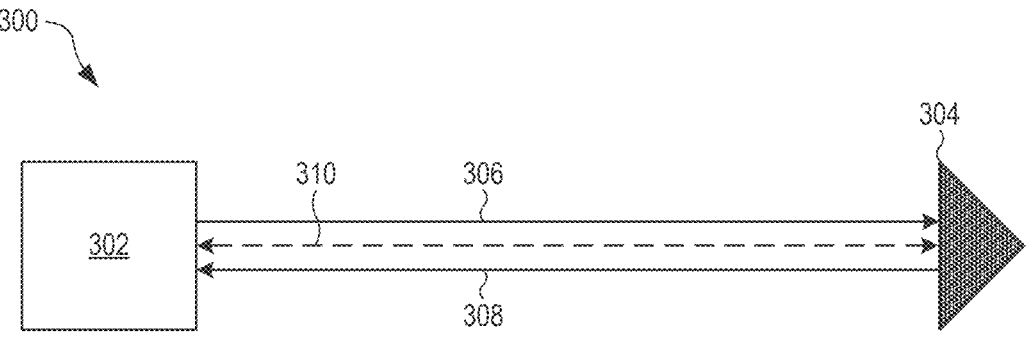
FIG. 3 shows a "straight-path" configuration for measuring gases with a single retroreflected laser beam, in an embodiment.

FIG. 3 shows a "straight-path" configuration 300 for measuring gases with a single retroreflected laser beam, in an embodiment. In FIG. 3, a laser spectrometer 302 transmits a laser beam 306 toward a retroreflector 304 that retroreflects the laser beam 306 into a retroreflected laser beam 308 that propagates back to the laser spectrometer 302, where it is detected. In FIG. 3, the laser beam 306 propagates directly between the laser spectrometer 302 and the retroreflector 304, i.e., the laser beam 306 propagates along a straight-line path 310 between the laser spectrometer 302 and the retroreflector 304 without passing through any intermediary optics or components (e.g., mirrors, lenses, modulators, prisms, etc.). Similarly, the retroreflected laser beam 308 propagates directly between the retroreflector 304 and the laser spectrometer 302 along the straight-line path 310. Thus, the laser beams 306 and 308 only propagate through gas.

FIGS. 1 and 2 show several instances of the straight-path configuration 300. The laser spectrometer 302 is one example of the optical spectrometer 116 of FIGS. 1 and 2. The retroreflectors 114(1) and 114(2) of FIG. 1 are examples of the retroreflector 304. While the retroreflector 304 is shown in FIG. 3 as a corner-cube retroreflector, another type of retroreflector may be used without departing from the scope here.

Figure 4:
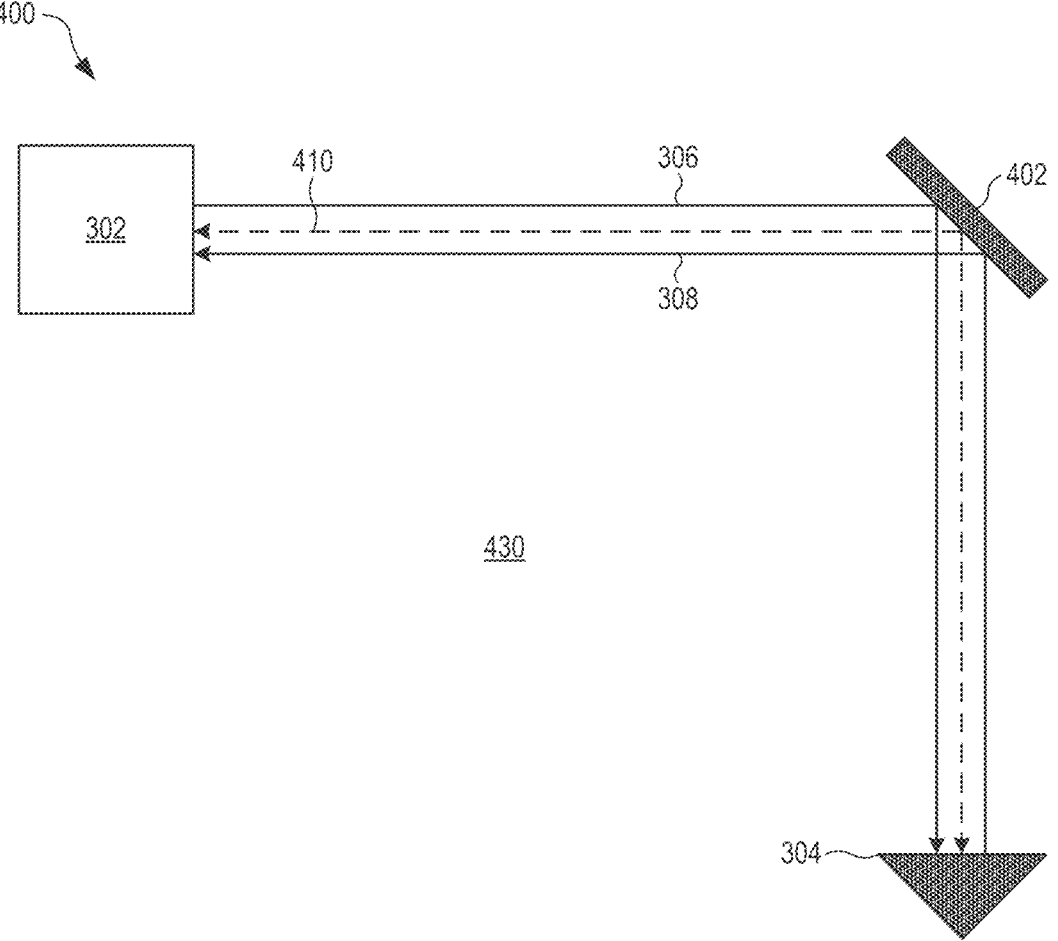
FIG. 4 shows a "piecewise-path" configuration for measuring gases with a single retroreflected laser beam, in an embodiment.

FIG. 4 shows a "piecewise-path" configuration 400 for measuring gases with a single retroreflected laser beam, in an embodiment. In FIG. 4, the laser spectrometer 302 directly transmits the laser beam 306 toward a steering mirror 402, which reflects the laser beam 306 directly toward the retroreflector 304. The retroreflector 304 retroreflects the laser beam 306 into a retroreflected laser beam 308 that directly propagates back toward the steering mirror 402, which then reflects the retroreflected laser beam 308 back toward the laser spectrometer 302, where it is detected. Thus, each of the laser beams 306 and 308 propagates along two "legs" of a piecewise path 410, each of the two legs having a different direction. In the example of FIG. 4, the steering mirror 402 reflects each of the laser beams 306 and 308 at a right angle. However, the steering mirror 402 and retroreflector 304 may be positioned such that the steering mirror 402 reflects each of the laser beams 306 and 308 by an angle other than 90 degrees. Furthermore, one or more additional steering mirrors 402 may be used to define the piecewise path 410.

Advantageously, the piecewise-path configuration 400 allows a longer perimeter of an area (e.g., the geographic area 130 of FIGS. 1 and 2) to be sampled. For example, in FIG. 4, the piecewise path 410 forms two adjacent sides of an area 430 that may be rectangular. Sampling over a longer perimeter improves the accuracy of (1) estimates of background inflow of air into the area 430, and (2) estimates of outflow of air from the area 430. With these improved estimates, the influence of point/area gas sources can be better constrained and/or constrained more rapidly.

Figure 5:
FIG. 5 shows an "area-enclosing-path" configuration for measuring gases with a single laser beam that is not retroreflected, in an embodiment.
Figure 5:
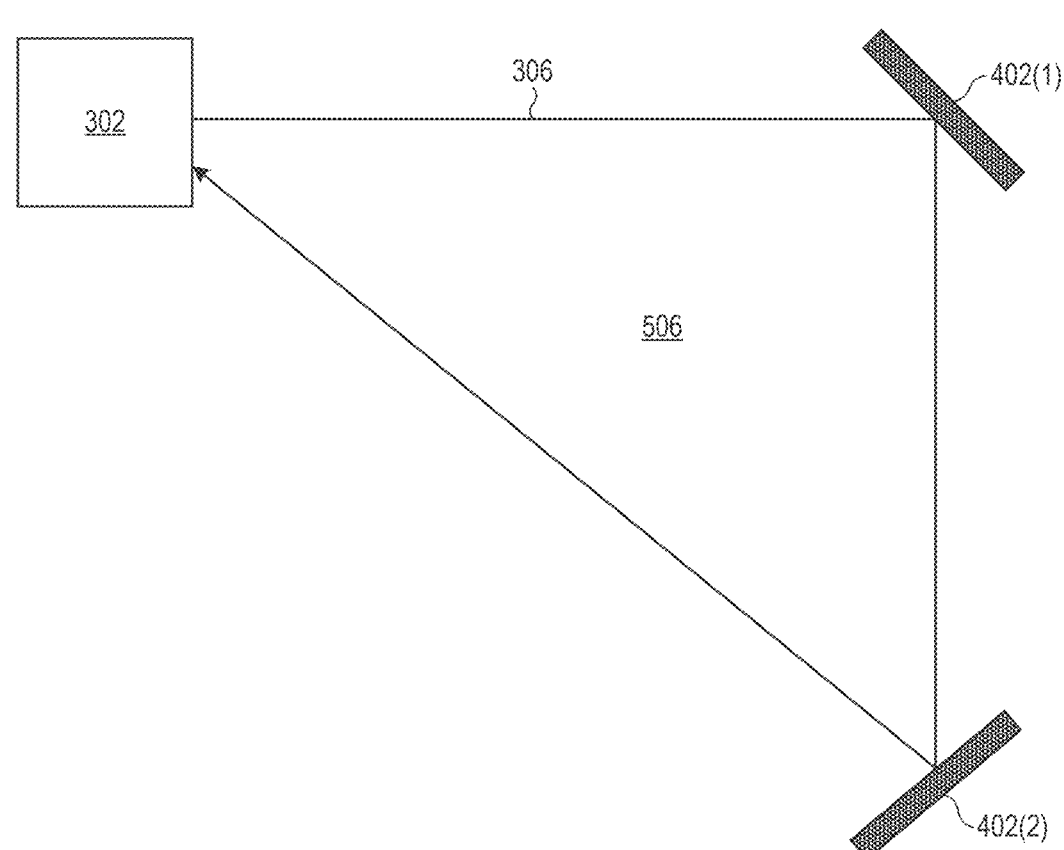

FIG. 5 shows an "area-enclosing-path" configuration 500 for measuring gases with a single laser beam that is not retroreflected, in an embodiment. The configuration 500 uses two or more mirrors 402 to steer the laser beam 306 along a piecewise path that encloses a polygonal-shaped area 506. While the example of FIG. 5 shows two mirrors 402(1), 402(2) used to define a triangular area 506, more than two mirrors 402 may be used to define a different type of polygon (e.g., rectangle, pentagon, etc.) without departing from the scope hereof.

Advantageously, the "area-enclosing-path" configuration 500 can be adapted to accommodate various shapes of the area 506, including oddly shaped areas (e.g., city blocks or complex industrial facilities) or areas having obstructions (e.g., terrain, vegetation, buildings) that may prevent the use of the "straight-path" configuration 300. The "area-enclosing-path" configuration 500 may also be used for "fenceline" monitoring of a facility. Fenceline monitoring is advantageous for detecting emissions from the facility since the laser beams completely surround the facility, and are therefore likely to detect emissions regardless of wind direction. Alternatively, fenceline monitoring can be used to detect gases entering the facility (i.e., originating outside of the area 506).

Figure 6:
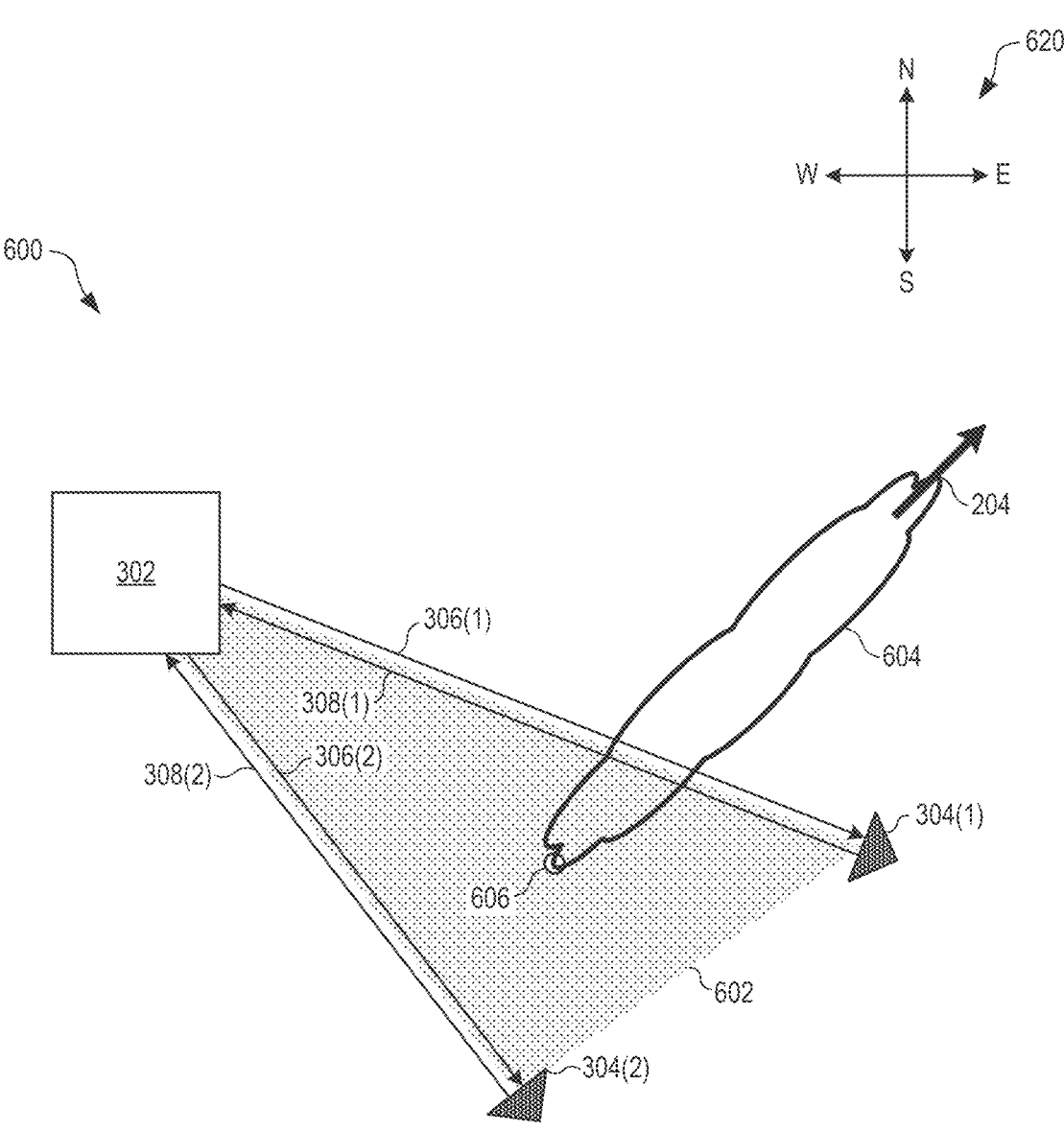
FIG. 6 shows a "wedge" configuration for measuring gases with two laser beams that are transmitted simultaneously from a single point, in an embodiment.

FIG. 6 shows a "wedge" configuration 600 for measuring gases with two laser beams that are transmitted simultaneously from a single point, in an embodiment. The configuration 600 uses the straight-line configuration 300 of FIG. 3 for each of first and second laser beams 306(1), 306(2) that are simultaneously transmitted by the laser spectrometer 302. A first retroreflector 304(1) retroreflects the first laser beam 306(1) into a first retroreflected laser beam 308(1) that directly propagates back to the laser spectrometer 302. Simultaneously, a second retroreflector 304(2) retroreflects the second laser beam 306(2) into a second retroreflected laser beam 308(2) that directly propagates back to the laser spectrometer 302. The laser spectrometer 302 measures the first and second retroreflected laser beams 308(1), 308(2) simultaneously to obtain first and second absorptions. An inversion may then be performed, based on the first and second absorptions, to determine emission characteristics of at least one gas species within a wedge-shaped area 602 bound by the laser beams 306(1), 306(2), 308(1), and 308(2).

As an example, the wedge configuration 600 may be used to sample each sector 102 in FIGS. 1 and 2. Similar to these sectors 102, the wedge-shaped area 602 may be considered a sector defined by two rays that originate at the laser spectrometer 302, and extend along the paths followed by the laser beams 306(1) and 306(2).

The wedge configuration 600 can advantageously detect a gas plume 604, emitted from an emission source 606 located within the area 602, when wind blows the plume 604 through only one of the two laser beams 306(1), 306(2). In the example of FIG. 6, the wind blows in a direction 204, causing the plume 604 to pass only through the first laser beam 306(1). As a result, the second laser beam 306(2) can be used to measure a background concentration, thereby improving the accuracy with which the flux of the plume 604 can be determined. Any wind condition that causes differential concentration patterns on the two laser beams 306(1) and 306(2) can be used to determine emission source characteristics. Similarly, gas sinks can be determined (the uptake of gas by processes in the wedge).

Sampling with both laser beams 306(1), 306(2) simultaneously provides several advantages over sampling sequentially. First, data can be obtained faster since there is no "dead time" between sequential measurements (e.g., the time required to move the gimbal mount 128). Without this dead time, more data can be collected over a given period of time, which increases signal-to-noise ratio, and hence sensitivity. Second, there is no time lag between the measurement of the downwind beam (i.e., the laser beam 306(1) in FIG. 6) and the upwind beam (i.e., the laser beam 306(2) in FIG. 6). As a result, there is better rejection of temporal variations in the background concentration since these temporal variations affect both beams simultaneously. This improved background rejection enhances the accuracy of the determined flux. Third, atmospheric modeling is simplified, further enhancing the accuracy of the determined flux.

Figure 7:
FIG. 7 shows a "box" configuration for fenceline monitoring of a rectangular area with two laser beams, in embodiments.
Figure 7:
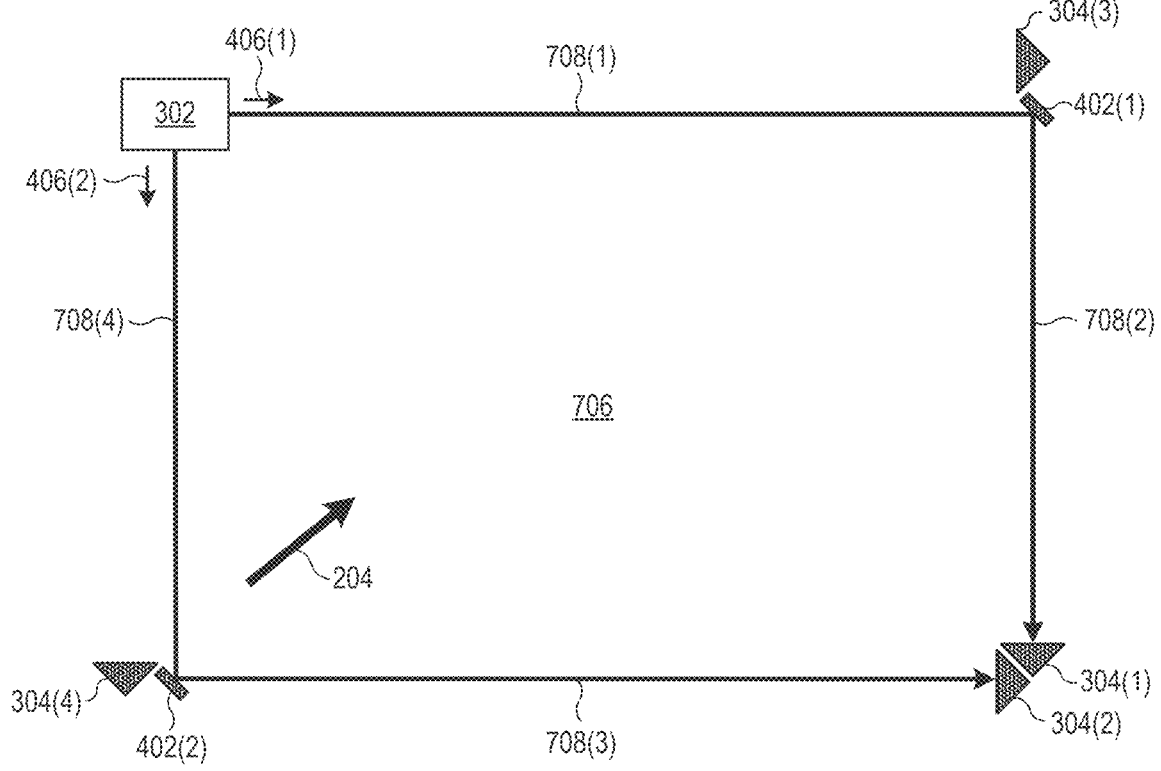
Figure 8:
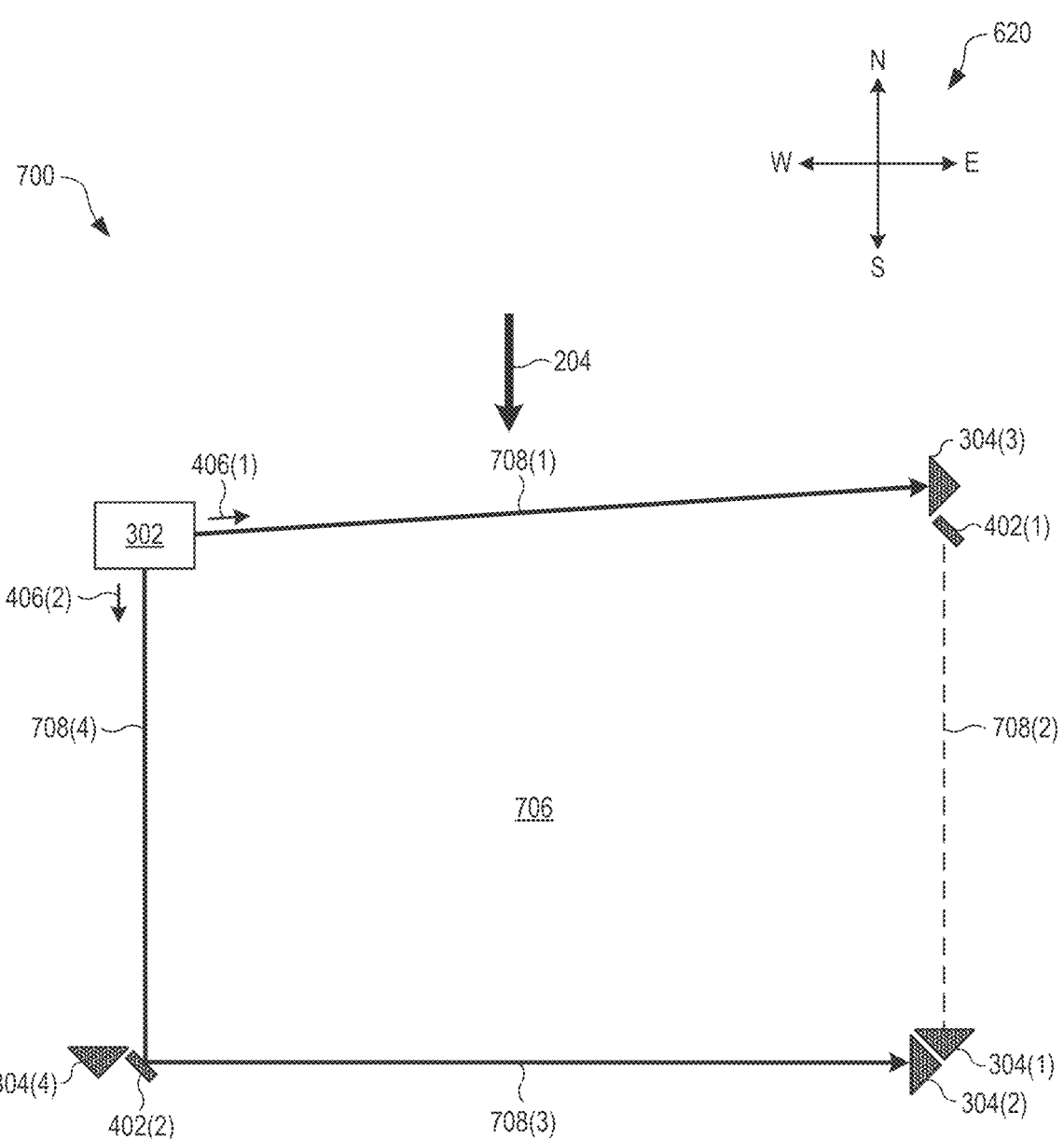
FIG. 8 shows how the box configuration of FIG. 7 can be used to sample only three sides of the rectangular area, in an embodiment.
Figure 9:
FIG. 9 shows another way to use the box configuration of FIG. 7 to sample three sides of the rectangular area, in an embodiment.
Figure 9:
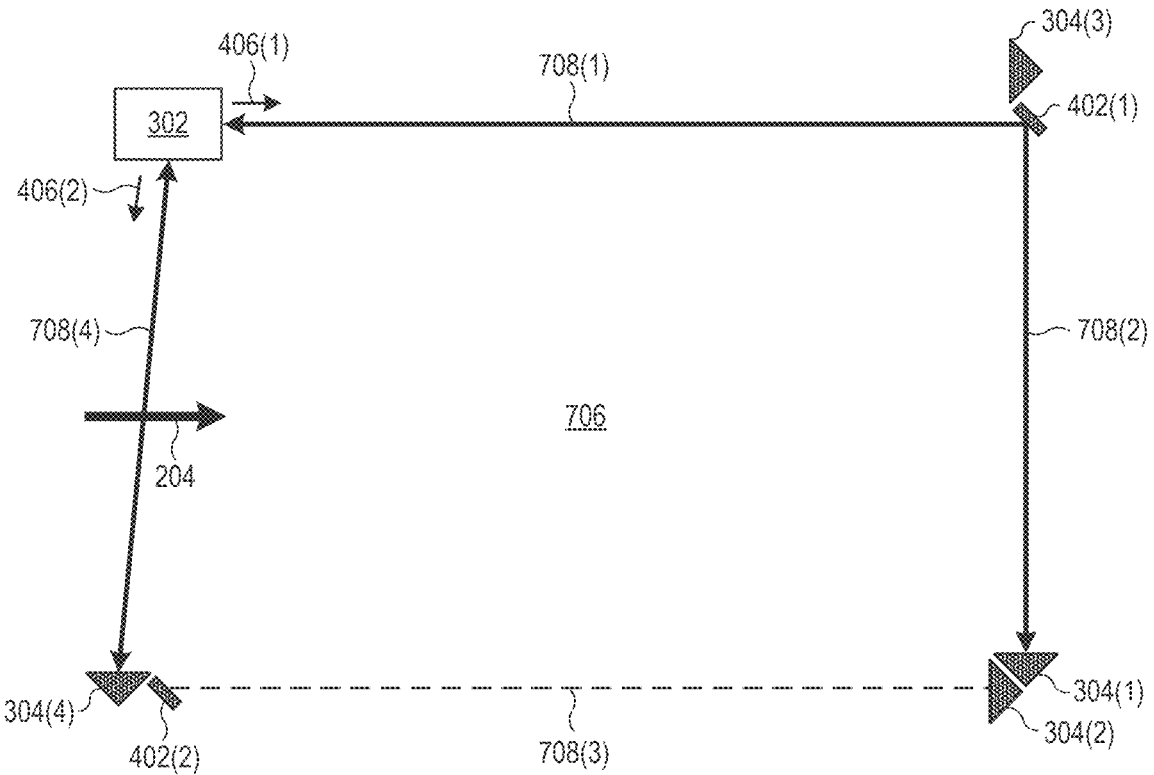

FIGS. 7-9 show a "box" configuration 700 for fenceline monitoring of a rectangular area 706 with two laser beams, in embodiments. FIG. 7 shows the box configuration 700 being used to sample the full perimeter of the rectangular area 706. FIGS. 8 and 9 show the box configuration 700 being used to sample only three sides of the rectangular area 706. FIGS. 7-9 are best viewed together with the following description.

Fenceline monitoring is advantageously used to monitor the full perimeter of an area. In the example of FIGS. 7-9, the rectangular area 706 is defined by four vertices, or corners. At the top-left corner, the laser spectrometer 302 simultaneously transmits first and second laser beams 406(1), 406(2) in orthogonal directions. The first laser beam 406(1) follows a first piecewise-path (e.g., see the piecewise-path configuration 400 of FIG. 4) formed from first and second legs 708(1), 708(2). The first and second legs 708(1), 708(2) are defined by a first mirror 402(1) located at the top-right corner of the rectangular area 706, and a first retroreflector 304(1) located at the bottom-right corner of the rectangular area 706. The first mirror 402(1) reflects the first laser beam 406(1) toward the first retroreflector 304(1), which retroreflects the first laser beam 406(1) back to the first mirror 402(1). The first mirror 402(1) then reflects the retroreflected first laser beam 406(1) back to the laser spectrometer 302, where it is detected. Similarly, the second laser beam 406(2) follows a second piecewise-path formed from third and fourth legs 708(3), 708(4). The third and fourth legs 708(3), 708(4) are defined by a second mirror 402(2) located at the bottom-left corner of the rectangular area 706, and a second retroreflector 304(2) located at the bottom-right corner.

Advantageously, the box configuration 700 can be used to simultaneously measure inflows and outflows for a wind coming from any of several different directions. In the example of FIG. 7, the wind is coming from the southwest (see compass 620), as indicated by the wind direction 204. In this case, the inflow of gas into the rectangular area 706 is best measured by sampling along the third and fourth legs 708(3), 708(4). These legs are also referred to as "upwind" legs. Similarly, the outflow of gas is best measured by sampling along the first and second legs 708(1), 708(2), which are also referred to as "downwind" legs. The example of FIG. 7 can also be used when the wind is coming from the northeast.

FIG. 8 shows how the box configuration 700 can be used to sample only three of the four legs of the rectangular area 706. Here, the laser spectrometer 302 directly transmits the first laser beam 406(1) to a third retroreflector 304(3) that directly retroreflects the first laser beam 406(1) back to the laser spectrometer 302, where it is detected (e.g., see the straight-path configuration 300 of FIG. 3). The third retrore-flector 304(3) is located proximate to the first mirror 402(1) so that the first laser beam 406(1) essentially samples only the first leg 708(1). The laser spectrometer 302 transmits and detects the second laser beam 406(2) similarly as in FIG. 7.

In the example of FIG. 8, the wind is coming from the north. Since little gas is expected to flow across the second leg 708(2), its exclusion from sampling allows for better constraint of inflow. In this case, the first leg 708(1) is an upwind leg. The example of FIG. 8 can also be used to better constrain outflow when the wind is coming from the south, in which case the first leg 708(1) is a downwind leg.

FIG. 9 shows another way to use the box configuration 700 to sample three of the four legs of the rectangular area 706. Here, the laser spectrometer 302 directly transmits the second laser beam 406(2) to a fourth retroreflector 304(4) that directly retroreflects the second laser beam 406(2) back to the laser spectrometer 302, where it is detected (e.g., see the straight-path configuration 300 of FIG. 3). The fourth retroreflector 304(4) is located proximate to the second mirror 402(2) so that the second laser beam 406(2) essentially samples only the fourth leg 708(4). The laser spec-trometer 302 transmits and detects the first laser beam 406(1) similarly as in FIG. 7.

In the example of FIG. 9, the wind is coming from the west. Since little gas is expected to flow across the third leg 708(3), its exclusion from sampling allows for better con-straint of inflow. In this case, the fourth leg 708(4) is an upwind leg. The example of FIG. 9 can also be used to better constrain outflow when the wind is coming from the east, in which case the fourth leg 708(4) is a downwind leg.

Advantageously, the box configuration 700 can monitor upwind and downwind legs simultaneously, thereby mea-suring changes in the characteristics of the incoming air quickly enough that effects can be accounted for in the downwind leg measurements. By monitoring winds in real-time, legs can be added or removed from the upwind and downwind laser-beam paths to accommodate changing wind conditions.

While FIGS. 7-9 show the area 706 as being rectangular, the box configuration 700 can be modified to enclose other types of polygons. For example, each of the first and second laser beams 406(1), 406(2) can propagate along a piecewise path formed with more than one mirror 402 to generate more than two legs. The resulting area 706 may be a regular or irregular triangle, pentagon, octagon, etc.

Figure 10:
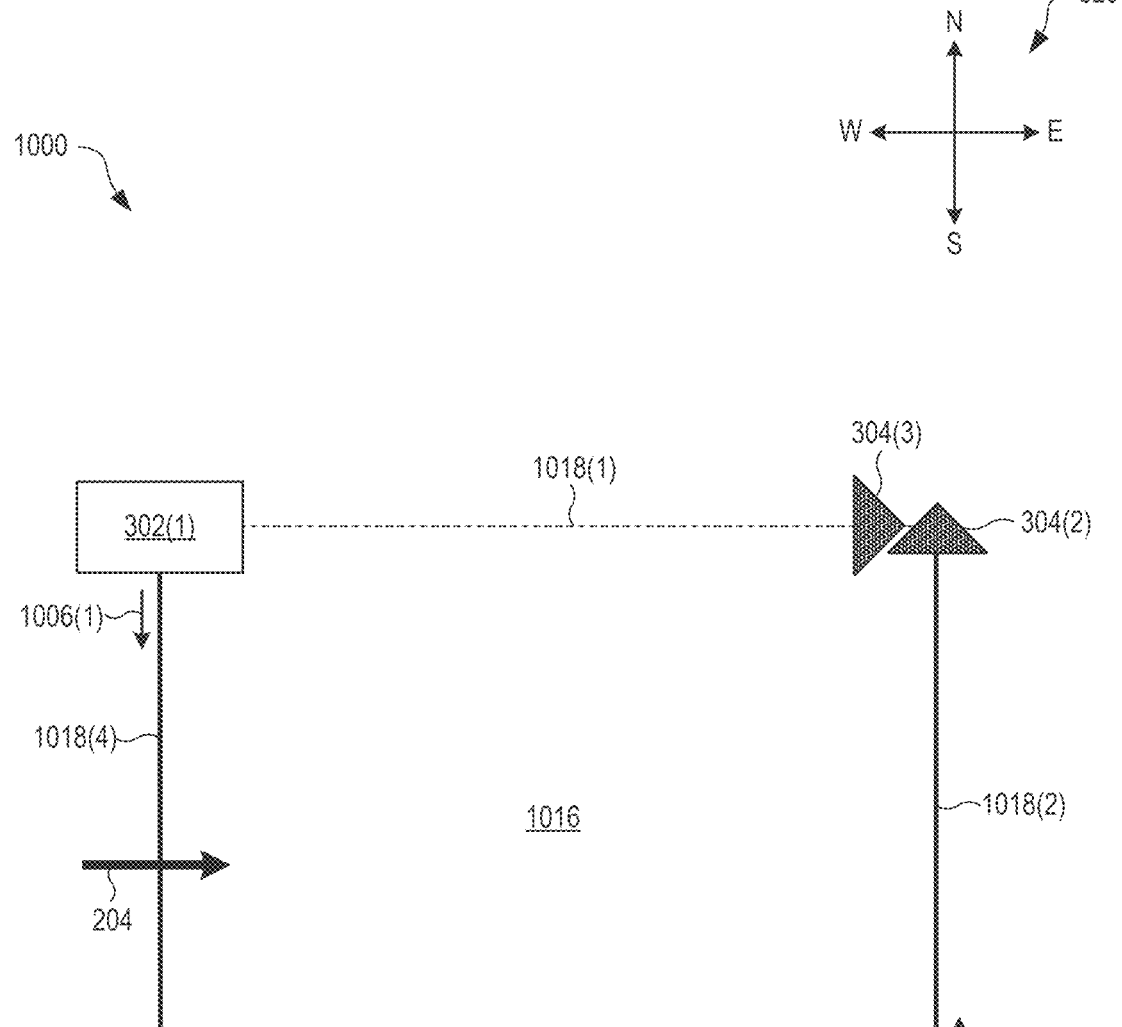
FIG. 10 shows a two-source "box" configuration for measuring gases with two laser beams that are transmitted simultaneously from two separate points, in an embodiment.

FIG. 10 shows a two-source "box" configuration 1000 for measuring gases with two laser beams that are transmitted simultaneously from two separate points, in an embodiment. A first laser spectrometer 302(1) transmits a first laser beam 1006(1) toward a first retroreflector 304(1) according to the straight-path configuration 300 of FIG. 3. The first laser beam 1006(1), and its reflection, propagate along a fourth leg 1018(4) of a rectangular area 1016. Similarly, a second laser spectrometer 302(2) transmits a second laser beam 1006(2) toward a second retroreflector 304(2), also accord-ing to the straight-path configuration 300. The second laser beam 1006(2), and its reflection, propagate along a second leg 1018(2) of the rectangular area 1016. The first and second laser spectrometers 302(1), 302(2) are located on opposite corners of the rectangular area 1016, and therefore the first and second laser beams 1006(1), 1006(2) propagate along parallel paths that are aligned in the north-south direction and displaced from each other in the east-west direction (see compass 620). In the example of FIG. 10, where the wind is coming from the west, the fourth leg 1018(4) is an upwind leg and the second leg 1018(2) is a downwind leg. If the wind were coming from the east, the fourth leg 1018(4) would be a downwind leg and the second leg 1018(2) would be an upwind leg.

Figure 11:
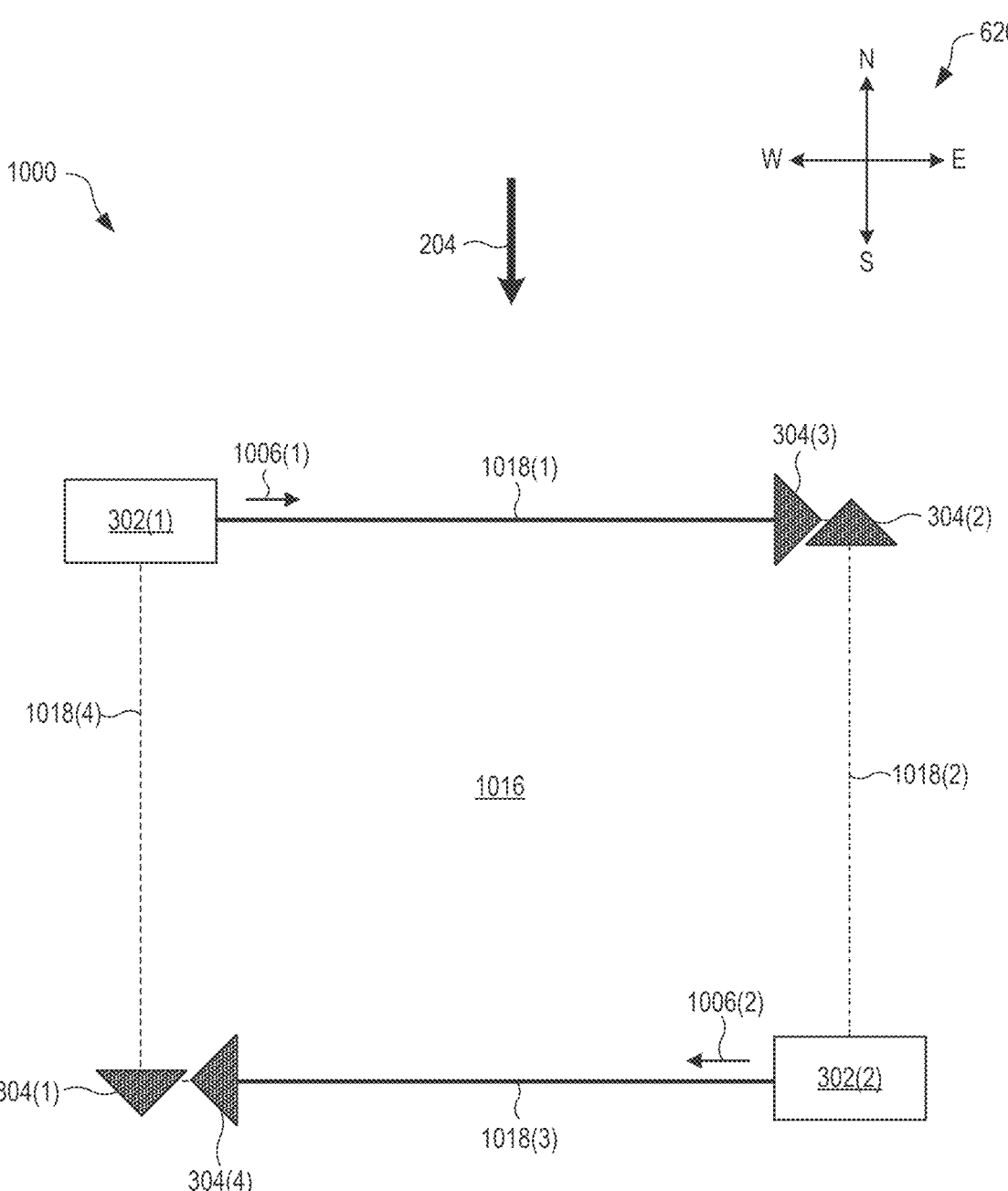
FIG. 11 shows how the two-source box configuration of FIG. 10 can be used when the wind comes from the north or south.

FIG. 11 shows how the two-source box configuration 1000 can be used when the wind comes from the north or south. In this case, the first laser spectrometer 302(1) trans-mits the first laser beam 1006(1) to a third retroreflector 304(3) that is located proximate to the second retroreflector 304(2) so that the first laser beam 1006(1) propagates along a first leg 1018(1) of the rectangular area 1016. Similarly, the second laser spectrometer 302(2) transmits the second laser beam 1006(2) to a fourth retroreflector 304(4) that is located proximate to the first retroreflector 304(1) so that the second laser beam 1006(2) propagates along a third leg 1018(3) of the rectangular area 1016. Therefore, the first and second laser beams 1006(1), 1006(2) propagate along parallel paths that are aligned in the east-west direction and displaced from each other in the north-south direction. In the example of FIG. 11, where the wind is coming from the north, the first leg 1018(1) is an upwind leg and the third leg 1018(3) is a downwind leg. If the wind were coming from the south, the first leg 1018(1) would be a downwind leg and the third leg 1018(3) would be an upwind leg.

Each of the laser spectrometers 302(1), 302(2) may be mounted to a gimbal (e.g., the gimbal mount 128 of FIGS. 1 and 2) to change the directions of the laser beams 1006(1), 1006(2), respectively. Alternatively, one laser spectrometer 302 outputting two laser beams simultaneously can be used in lieu of the two separate laser spectrometers 302(1), 302(2). In this case, the two laser beams can be transmitted (e.g., via fiber-optic cables) to the top-left and bottom-right corners of the area 1016, where they are launched as free-space laser beams 1006(1), 1006(2) using coupling optics mounted to gimbals.

Advantageously, the two-source box configuration 1000 samples upwind and downwind legs 1018 simultaneously, which improves signal-to-noise ratio by eliminating time gaps, as compared to measuring the legs 1018 sequentially. By changing the directions of the laser beams 1006(1), 1006(2), the two-source box configuration 1000 can be quickly and readily modified in response to changes in the wind direction 204. Furthermore, very large areas can be monitored in a mass balance. For example, each of the four legs 1018 may be 4 km, in which case the rectangular area 1016 has an area of 16 km$^2$.

Figure 12:
FIG. 12 shows another two-source box configuration that is similar to the two-source box configuration of FIGS. 10 and 11, in an embodiment.
Figure 12:
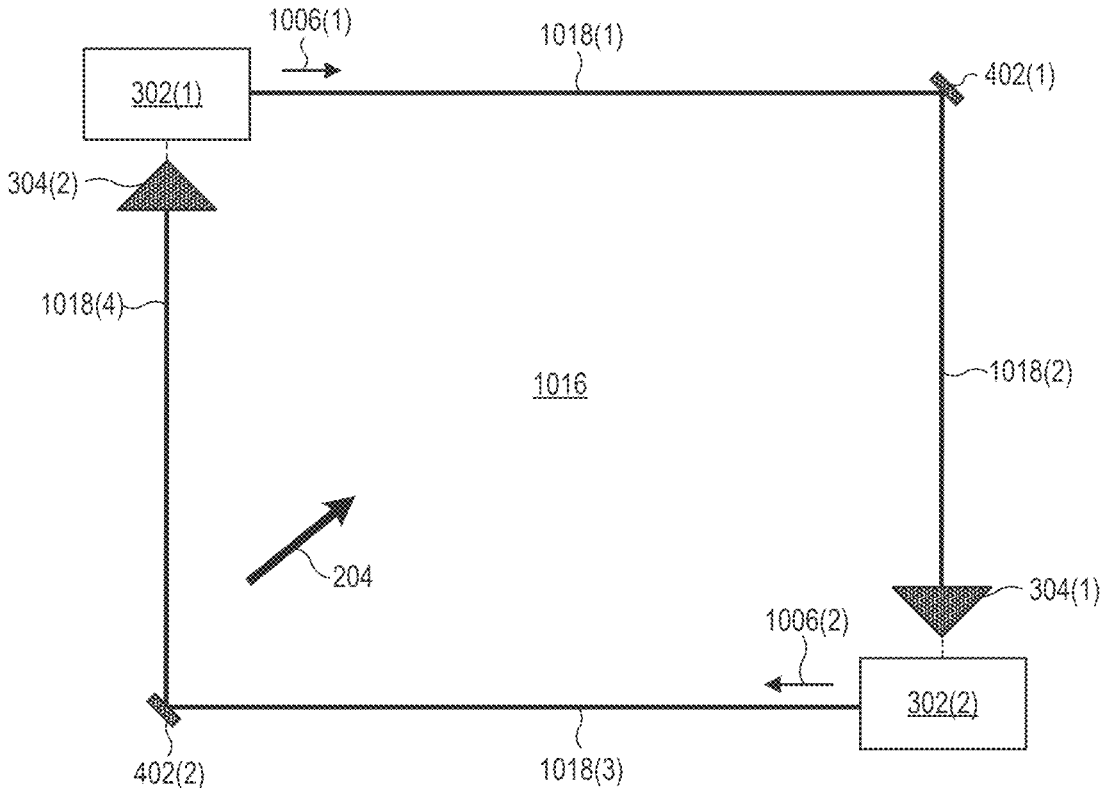

FIG. 12 shows another two-source box configuration 1200 that is similar to the two-source box configuration 1000 of FIGS. 10 and 11 except that each of the laser beams 1006(1), 1006(2) propagates along a piecewise path formed from two adjacent legs 1018 of the rectangular area 1016, in embodiments. The two-source box configuration 1200 has similar advantages to the box configuration 700, as shown in FIG. 7, i.e., inflows and outflows can be measured simultaneously for a wind coming from a diagonal direction (e.g., the southwest in FIG. 12).

In an embodiment, the two-source box configuration 1200 uses additional retroreflectors 304 located at the top-right and bottom-left corners of the rectangular area 1016, i.e., proximate to the mirrors 402(1) and 402(2). With these additional retroreflectors 304, the first laser beam 1006(1) can be additionally steered according to a straight-path configuration along the first leg 1018(1) or the fourth leg 1018(4), similar to the two-source box configuration 1000 of FIGS. 10 and 11. The second laser beam 1006(2) can be additionally steered according to a straight-path configuration along the second leg 1018(2) or the third leg 1018(3), also similar to the two-source box configuration 1000. This embodiment therefore combines the functionality of the two-source box configuration 1000 with the box configuration 700 of FIG. 7.

While FIGS. 10-12 show the area 1016 as being rectangular, the two-source box configurations 1000 and 1200 can be modified to enclose other types of polygons. For example, each of the first and second laser beams 1006(1), 1006(2) can propagate along a piecewise path formed with more than one mirror 402 to generate more than two legs. The resulting area 1016 may be a regular or irregular triangle, pentagon, octagon, etc.

The two-source box configurations 1000 and 1200 may be used for tomography of trace gas concentrations. When each of the laser spectrometers 302(1) and 302(2) is a dual frequency-comb spectrometer, no calibration between the laser spectrometers 302(1) and 302(2) is required, advantageously extending how long continuous measurements can be obtained and providing higher fidelity of concentration and source information. By comparison, other types of laser spectrometer 302 that drift require frequent calibration.

In the preceding discussion, many of the embodiments have been described as using retroreflectors that retroreflect an incoming laser beam into a retroreflected laser beam that propagates back to the laser spectrometer, where it is detected. In other embodiments, each retroreflector is replaced by another type of optic that redirects at least part of the incoming laser beam into a counterpropagating laser beam that propagates back to the laser spectrometer for detection. This counterpropagating laser beam acts like the retroreflected laser beam described above in that it traverses the same path as the incoming laser beam, but in the opposite direction. For example, a diffraction grating may be used in place of a mirror, wherein one of the diffraction orders serves as the counterpropagating laser beam (the other orders may be either discarded or used for a different purpose). In another example, the incoming laser beam strikes a surface that scatters that incoming laser beam. In this case, some of the scattered light propagates back to the laser spectrometer, where it may be detected similarly to the retroreflected laser beam. Any other type of optic or optical setup may be used to generate counterpropagating light for detection without departing from the scope hereof.

Find-and-Fix Detection

A method determines if emissions at a site (e.g., a pad 104) exceed an emissions threshold, or if a type of event has occurred at the site with a probability exceeding a probability threshold, in embodiments. This method may be used, for example, to detect aberrations from baseline emissions. In some embodiments, the output of the method is a numerical, descriptive, or colored indication, e.g., "red" indicating that the emissions probability exceeds an upper probability threshold, "green" indicating that the emissions probability is less than a lower probability threshold, and "yellow" indicating that the emissions probability is between the upper and lower probability thresholds.

The colored indication is one example of an outputted flag or event that advantageously allows a user to more quickly identify whether an action is to be performed. By comparison, an outputted quantitative data stream may not be as easily actionable, therefore delaying time-sensitive fixes to, for example, broken equipment. For example, the method may be used to quickly determine that a large emission is not present.

The method uses quantified detection thresholds, i.e., emission thresholds that are either pre-selected (e.g., set beforehand) or iterative (e.g., evolve with, for example, the aid of machine learning) to provide "detection" limits and triggers for "find-and-fix" activities.

In some embodiments, the method uses machine learning/ artificial intelligence approaches. For example, historical emissions data on various events (e.g., a particular type of failure or design flaw on system that led to a particular time series of emissions data) could be used as training data for ML/AI approaches that would flag the most likely causes for new events.

As an example of quantifying the detection thresholds without machine learning, one can identify "problematic" emissions from a statistical standpoint by looking to scientific literature and field studies. For example, if the goal is to reduce overall emissions by 80%, then one could look to field observations documented in the literature and find which rates of emissions cause that percentage of emissions. Emissions distributions are typically fat-tailed, wherein very large and infrequent emission events contribute disproportionately to overall total emissions. Therefore, one could identify a target emission reduction and then use the literature to find the size (rate) event that contributes that percentage of overall emissions.

An example of training data that could be used for machine-learning is historical "finds" with the gas detector (e.g., the optical gas detector 100 of FIGS. 1 and 2), a dual frequency-comb observation system, or another type of gas monitor. For example, emissions data collected with such monitoring systems can be combined with information from operators, such as line pressures associated with the emitting area. When a large emission event occurs, and is identified by the monitoring system, a team may then be dispatched to the field to diagnose the problem (e.g., improper venting due to a broken seal). After diagnosis, the data (i.e., the history of the line pressures combined with the history of emissions) can be used as supervisory training data to update a machine-learning model (e.g., backpropagation of a neural network).

For clarity herein, many of the present embodiments are described in terms of laser beams (e.g., the laser beams 106(1) and 106(2) of FIGS. 1 and 2) and laser-based spectrometers (e.g., the laser spectrometer 302 of FIG. 3). However, it should be understood that any of the present embodiments—including the straight-path configuration 300, the piecewise-path configuration 400, the area-enclosing-path configuration 500, the wedge configuration 600, the box configuration 700, the two-source box configuration 1000, and the two-source box configuration 1200—may be alternatively implemented using any type of optical beam known in the art. The term "optical beam" is used herein to refer to any type of collimated light, either coherent or incoherent, that can be used for absorption measurements. Thus, any one or more of the laser beams 106(1), 106(2), 306, 406(1), 406(2), 1006(1), and 1006(2) may be an optical beam without departing from the scope hereof. Accordingly, any one or more of the retroreflected laser beams 308 may also be an optical beam. In any embodiment using an optical beam that is incoherent, the incoherent optical beam may be generated from any incoherent light source known in the art (e.g., a lamp, light-emitting diode, discharge tube, etc.) and collimated using known optical components and beam-forming techniques (e.g., lenses). Alternatively, the incoherent light beam may be generated by collimating sunlight. In this case, absorption of the sunlight may be detected using a laser heterodyne radiometer, which is one example of an optical spectrometer. Another type of optical spectrometer may be used with any of the present embodiments without departing from the scope hereof.

Combinations of Features

Features described above as well as those claimed below may be combined in various ways without departing from the scope hereof. The following examples illustrate possible, non-limiting combinations of features and embodiments described above. It should be clear that other changes and modifications may be made to the present embodiments without departing from the spirit and scope of this invention:

(A1) A method for characterizing gas emissions includes sampling each of a plurality of sectors having a common geographic center. Said sampling includes measuring first absorption of a first optical beam that is transmitted from the geographic center and retroreflected at a first retroreflection location within said each of the plurality of sectors. Said sampling also includes measuring second absorption of a second optical beam that is transmitted from the geographic center and retroreflected at a second retroreflection location within said each of the plurality of sectors. Said sampling also includes determining first and second concentrations based on the first and second absorptions, respectively. Said sampling also includes determining emission information based on the first and second concentrations.

(A2) In the method denoted (A1), for each of the plurality of sectors, the first and second optical beams are located on opposite sides of a potential gas source.

(A3) In either of the methods denoted (A1) and (A2), a duration of said measuring the first absorption and said measuring the second absorption is similar for all of the plurality of sectors.

(A4) In any of the methods denoted (A1)-(A3), a duration of said measuring the first absorption and said measuring the second absorption is different for each of the plurality of sectors.

(A5) In any of the methods denoted (A1)-(A4), said measuring the first absorption includes transmitting the first optical beam from a spectrometer located at the geographic center and detecting the retroreflected first optical beam with the spectrometer. Said measuring the second absorption includes transmitting the second optical beam from the spectrometer and detecting the retroreflected second optical beam with the spectrometer.

(A6) In the method denoted (A5), the spectrometer is one of a dual-frequency-comb spectrometer and a single-frequency laser spectrometer.

(A7) In any of the methods denoted (A1)-(A6), the method further includes selecting the plurality of sectors from a geographical area that includes the geographic center. The method further includes determining, for each of the plurality of sectors, a first transmission direction of the first optical beam from the geographic center to the first retroreflection location, and a second transmission direction of the second optical beam from the geographic center to the second retroreflection location.

(A8) In the method denoted (A7), the method further includes positioning, for each of the plurality of sectors, first and second retroreflectors at the first and second retroreflection locations, respectively.

(A9) In either of the methods denoted (A7) and (A8), each of the plurality of sectors at least partially overlaps a target location located within the geographical area.

(B1) A method for characterizing gas emissions includes sampling a first sector azimuthally bounded by first and second rays originating at a center point. Said sampling the first sector includes (i) steering a gimbal mount to transmit a first optical beam along the first ray, (ii) retroreflecting the first optical beam back toward the center point, (iii) measuring, after said retroreflecting the first optical beam, first absorption of the first optical beam, (iv) steering the gimbal mount to transmit a second optical beam along the second ray, (v) retroreflecting the second optical beam back toward the center point, (vi) measuring, after said retroreflecting the second optical beam, second absorption of the second optical beam, and (vii) performing a first inversion, based on the first and second absorptions, to determine emission characteristics of at least one gas species within the first sector. The method also includes sampling a second sector azimuthally bounded by third and fourth rays originating at the center point. Said sampling the second sector includes (i) steering the gimbal mount to transmit a third optical beam along the third ray, (ii) retroreflecting the third optical beam back to the center point, (iii) measuring, after said retroreflecting the third optical beam, third absorption of the third optical beam, (iv) steering the gimbal mount to transmit a fourth optical beam along the fourth ray, (v) retroreflecting the fourth optical beam back to the center point, (vi) measuring, after said retroreflecting the fourth optical beam, fourth absorption of the fourth optical beam, and (vii) performing a second inversion, based on the third and fourth absorptions, to determine emission characteristics of at least one gas species within the second sector.

(B2) In the method denoted (B1), the first and second sectors do not azimuthally overlap.

(B3) In either of the methods denoted (B1) and (B2), said measuring the first absorption includes detecting the first optical beam with a spectrometer located near the center point, said measuring the second absorption includes detecting the second optical beam with the spectrometer, said measuring the third absorption includes detecting the third optical beam with the spectrometer, and said measuring the fourth absorption includes detecting the fourth optical beam with the spectrometer.

(B4) In the method denoted (B3), the spectrometer is one of a dual-frequency-comb spectrometer and a single-frequency laser spectrometer.

(B5) In either of the methods denoted (B3) and (B4), the method further includes transmitting each of the first, second, third, and fourth optical beams with the spectrometer.

(C1) A method for characterizing gas emissions includes simultaneously transmitting first and second optical beams from a center point along respective first and second rays. The method also includes simultaneously retroreflecting the first and second optical beams into first and second retroreflected optical beams, respectively, that propagate back toward the center point. The method also includes simultaneously measuring first and second absorptions of the first and second retroreflected optical beams. The method also includes performing an inversion, based on the first and second absorptions, to determine emission characteristics of at least one gas species within an area bounded by the first and second optical beams.

(C2) In the method denoted (C1), simultaneously measuring includes simultaneously (i) detecting the first retroreflected optical beam with a first spectrometer located near the center point and (ii) detecting the second retroreflected optical beam with a second spectrometer located near the center point.

(C3) In the method denoted (C2), each of the first and second spectrometers is one of a dual-frequency-comb spectrometer and a single-frequency laser spectrometer.

(C4) In either of the methods denoted (C2) and (C3), the method further includes transmitting the first optical beam with the first spectrometer and transmitting the second optical beam with the second spectrometer.

(D1) A method for characterizing gas emissions includes transmitting a first optical beam from a center point along a first ray and reflecting, with at least one first mirror, the first optical beam toward a first retroreflector. The method also includes retroreflecting, with the first retroreflector, the first optical beam into a first retroreflected optical beam that reflects off the at least one first mirror to propagate back toward the center point. The method also includes measuring a first absorption of the first retroreflected optical beam.

(D2) In the method denoted (D1), the at least one first mirror comprises two or more first mirrors.

(D3) In either of the methods denoted (D1) and (D2), the at least one first mirror reflects the first optical beam along a first direction perpendicular to the first ray.

(D4) In the method denoted (D3), the method further includes transmitting a second optical beam from the center point along a second ray perpendicular to the first ray. The method also includes reflecting, with at least one second mirror, the second optical beam toward a second retroreflector along a second direction perpendicular to the second ray such that the first and second optical beams enclose a monitored area. The method also includes retroreflecting, with the second retroreflector, the second optical beam into a second retroreflected optical beam that reflects off the at least one second mirror to propagate back toward the center point. The method also includes measuring a second absorption of the second retroreflected optical beam.

(D5) In any of the methods denoted (D1)-(D4), the method further includes performing an inversion, based on the first and second absorptions, to determine emission characteristics of at least one gas species within the monitored area.

(D6) In any of the methods denoted (D1)-(D5), said measuring the first absorption includes detecting the first retroreflected optical beam with a spectrometer located near the center point. Furthermore, said measuring the second absorption includes detecting the second retroreflected optical beam with the spectrometer.

(D7) In the method denoted (D6), the spectrometer is one of a dual-frequency-comb spectrometer and a single-frequency laser spectrometer.

(D8) In either one of the methods denoted (D6) and (D7), said transmitting the first optical beam includes transmitting the first optical beam from the spectrometer. Furthermore, said transmitting the second optical beam includes transmitting the second optical beam from the spectrometer.

(D9) In any one of the methods denoted (D4)-(D8), the method includes transmitting a third optical beam from the center point along a third ray to a third retroreflector. The method further includes retroreflecting, with the third retroreflector, the third optical beam into a third retroreflected optical beam that propagates back toward the center point. The method further includes measuring a third absorption of the third retroreflected optical beam.

(D10) In the method denoted (D9), an angle between the first and third rays is less than five degrees.

(E1) A method for characterizing gas emissions includes transmitting a first optical beam from a first center point along a first ray, transmitting a second optical beam from a second center point along a second ray that is parallel to the first ray, retroreflecting the first optical beam into a first retroreflected optical beam that propagates back toward the first center point, retroreflecting the second optical beam into a second retroreflected optical beam that propagates back toward the second center point, measuring first absorption of the first retroreflected optical beam, and measuring second absorption of the second retroreflected optical beam.

(E2) In the method denoted (E1), the method further includes performing an inversion, based on the first and second absorptions, to determine emission characteristics of at least one gas species within an area at least partially bounded by the first and second rays.

(E3) In either of the methods denoted (E1) and (E2), said measuring the first absorption includes detecting the first retroreflected optical beam with a first spectrometer located near the first center point. Furthermore, said measuring the second absorption includes detecting the second retroreflected optical beam with a second spectrometer located near the second center point.

(E4) In the method denoted (E3), each of the first and second spectrometers is one of a dual-frequency-comb spectrometer and a single-frequency laser spectrometer.

(F1) A method for characterizing gas emissions includes simultaneously (i) transmitting a first optical beam from a first center point along a first ray, (ii) transmitting a second optical beam from a second center point along a second ray that is antiparallel to the first ray, (iii) reflecting, with a first mirror, the first optical beam toward the second center point, (iv) reflecting, with a second mirror, the second optical beam toward the first center point, (v) retroreflecting, with a first retroreflector located near the second center point, the first optical beam into a first retroreflected optical beam that reflects off the first mirror to propagate back toward the first center point, (vi) retroreflecting, with a second retroreflector located near the first center point, the second optical beam into a second retroreflected optical beam that reflects off the second mirror to propagate back toward the second center point, (vii) measuring a first absorption of the first retroreflected optical beam, and (viii) measuring a second absorption of the second retroreflected optical beam.

(F2) In the method denoted (F1), the method further includes performing an inversion, based on the first and second absorptions, to determine emission characteristics of at least one gas species within an area bounded by the first and second optical beams.

(F3) In either of the methods denoted (F1) and (F2), said measuring the first absorption includes detecting the first retroreflected optical beam with a first spectrometer located near the first center point. Furthermore, said measuring the second absorption includes detecting the second retroreflected optical beam with a second spectrometer located near the second center point.

(F4) In the method denoted (F3), each of the first and second spectrometers is one of a dual-frequency-comb spectrometer and a single-frequency laser spectrometer.

(F5) In either of the methods denoted (F3) and (F4), said transmitting the first optical beam includes transmitting the first optical beam from the first spectrometer. Furthermore, said transmitting the second optical beam includes transmitting the second optical beam from the second spectrometer.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method for characterizing gas emissions, comprising:
transmitting, with a first spectrometer, a first optical beam along a first path;
retroreflecting the first optical beam into a first retroreflected optical beam that propagates back toward the first spectrometer;
measuring the first retroreflected optical beam with the first spectrometer to generate a first absorption signal;
transmitting, with a second spectrometer, a second optical beam along a second path;
retroreflecting the second optical beam into a second retroreflected optical beam that propagates back toward the second spectrometer;
measuring the second retroreflected optical beam with the second spectrometer to generate a second absorption signal;
transmitting, with a third spectrometer, a third optical beam along a third path;
retroreflecting the third optical beam into a third retroreflected optical beam that propagates back toward the third spectrometer;
measuring the third retroreflected optical beam with the third spectrometer to generate a third absorption signal;
transmitting, with a fourth spectrometer, a fourth optical beam along a fourth path;
retroreflecting the fourth optical beam into a fourth retroreflected optical beam that propagates back toward the fourth spectrometer;
measuring the fourth retroreflected optical beam with the fourth spectrometer to generate a fourth absorption signal; and
determining one or more emission characteristics of at least one gas species within an area that is at least partially bounded by the first path, the second path, the third path, and the fourth path.

2. The method of claim 1, wherein:
said transmitting the third optical beam is performed by the first spectrometer;
the third retroreflected optical beam propagates back toward the first spectrometer; and
said measuring the third retroreflected optical beam is performed by the first spectrometer.

3. The method of claim 2, wherein:
said transmitting the fourth optical beam is performed by the second spectrometer;
the fourth retroreflected optical beam propagates back toward the second spectrometer; and
said measuring the fourth retroreflected optical beam is performed by the second spectrometer.

4. The method of claim 3, wherein:
said transmitting the first optical beam comprises transmitting the first optical beam from a first spectrometer location to a first retroreflection location, the first spectrometer being located at the first spectrometer location;
said retroreflecting the first optical beam comprises retroreflecting the first optical beam at the first retroreflection location;
said transmitting the second optical beam comprises transmitting the second optical beam from a second spectrometer location to a second retroreflection location, the second spectrometer being located at the second spectrometer location;
said retroreflecting the second optical beam comprises retroreflecting the second optical beam at the second retroreflection location;
said transmitting the third optical beam comprises transmitting the third optical beam from the first spectrometer location to a third retroreflection location;
said retroreflecting the third optical beam comprises retroreflecting the third optical beam at the third retroreflection location;
said transmitting the fourth optical beam comprises transmitting the fourth optical beam from the second spectrometer location to a fourth retroreflection location; and
said retroreflecting the fourth optical beam comprises retroreflecting the fourth optical beam at the fourth retroreflection location.

5. The method of claim 4, wherein:
said retroreflecting the first optical beam comprises retroreflecting the first optical beam with a first retroreflector located at the first retroreflection location;
said retroreflecting the second optical beam comprises retroreflecting the second optical beam with a second retroreflector located at the second retroreflection location;
said retroreflecting the third optical beam comprises retroreflecting the third optical beam with a third retroreflector located at the third retroreflection location; and
said retroreflecting the fourth optical beam comprises retroreflecting the fourth optical beam with a fourth retroreflector located at the fourth retroreflection location.

6. The method of claim 4, wherein one or both of:
the first retroreflection location is proximate the second retroreflection location; and
the third retroreflection location is proximate the fourth retroreflection location.

7. The method of claim 4, wherein one or both of:

the first retroreflection location is proximate the fourth retroreflection location; and the third retroreflection location is proximate the second retroreflection location.

8. The method of claim 3, wherein:

said transmitting the first optical beam and said transmitting the second optical beam occur simultaneously;

said retroreflecting the first optical beam and said retroreflecting the second optical beam occur simultaneously; and said measuring the first retroreflected optical beam and said measuring the second retroreflected optical beam occur simultaneously.

9. The method of claim 3, wherein:

said transmitting the third optical beam and said transmitting the fourth optical beam occur simultaneously;

said retroreflecting the third optical beam and said retroreflecting the fourth optical beam occur simultaneously; and said measuring the third retroreflected optical beam and said measuring the fourth retroreflected optical beam occur simultaneously.

10. The method of claim 1, the area being shaped as a quadrilateral.

11. The method of claim 10, the quadrilateral being a parallelogram.

12. The method of claim 11, the quadrilateral being a rectangle.

13. The method of claim 1, wherein one or both of:

the first path being parallel to the second path; and the third path being parallel to the fourth path.

14. The method of claim 1, wherein one or both of:

the first path being perpendicular to the second path; and the third path being perpendicular to the fourth path.

15. The method of claim 1, wherein:

said transmitting the first optical beam, said transmitting the second optical beam, said transmitting the third optical beam, and said transmitting the fourth optical beam occur simultaneously;

said retroreflecting the first optical beam, said retroreflecting the second optical beam, said retroreflecting the third optical beam, and said retroreflecting the fourth optical beam occur simultaneously; and said measuring the first retroreflected optical beam, said measuring the second retroreflected optical beam, said measuring the third retroreflected optical beam, and said measuring the fourth retroreflected optical beam occur simultaneously.

16. The method of claim 1, wherein said determining the one or more emission characteristics comprises performing tomography of trace gas concentrations within the area.

17. The method of claim 1, wherein said determining comprises performing an inversion.

18. The method of claim 1, wherein:

said transmitting with the first spectrometer comprises transmitting with a first dual-frequency-comb spectrometer or a first single-frequency laser spectrometer;

said transmitting with the second spectrometer comprises transmitting with a second dual-frequency-comb spectrometer or a second single-frequency laser spectrometer;

said transmitting with the third spectrometer comprises transmitting with a third dual-frequency-comb spectrometer or a third single-frequency laser spectrometer; and said transmitting with the fourth spectrometer comprises transmitting with a fourth dual-frequency-comb spectrometer or a fourth single-frequency laser spectrometer.

19. The method of claim 1, further comprising one or more of:

calibrating the first spectrometer;

calibrating the second spectrometer;

calibrating the third spectrometer; and calibrating the fourth spectrometer.

\* \* \* \* \*